United States Patent [19]
Beck et al.

[11] Patent Number: 5,659,098
[45] Date of Patent: *Aug. 19, 1997

[54] HIGH CONVERSION TOLUENE DISPROPORTIONATION WITH EX SITU SELECTIVATED ZEOLITE CATALYSTS

[76] Inventors: Jeffrey S. Beck, 2411 Town Run North, Lawrenceville, N.J. 08648; Timothy F. Kinn, 120 F. Hemlock Ct., Narraticon, Deptford, N.J. 08096; Sharon B. McCullen, 119 Colonial Dr., Newtown, Pa. 18940-1103; David H. Olson, 11 Morningside Dr., Hopewell Twp., Pennington, N.J. 08534-3108; David L. Stern, 2411 Town Court N., Lawrenceville, N.J. 08648

[*] Notice: The term of this patent shall not extend beyond the expiration date of Pat. No. 5,349,113.

[21] Appl. No.: 558,312

[22] Filed: Nov. 15, 1995

Related U.S. Application Data

[63] Continuation-in-part of Ser. No. 453,042, May 30, 1995, and Ser. No. 338,297, Nov. 14, 1994, Pat. No. 5,495,059, which is a division of Ser. No. 69,255, May 28, 1993, Pat. No. 5,403,800, said Ser. No. 453,042, is a division of Ser. No. 69,251, May 28, 1993, Pat. No. 5,476,823.

[51] Int. Cl.$^6$ .................................................. C07C 5/52
[52] U.S. Cl. .......................... 585/475; 585/467; 585/481; 585/470
[58] Field of Search .................... 585/475, 467, 585/481, 470

[56] References Cited

U.S. PATENT DOCUMENTS

| | | |
|---|---|---|
| 3,251,897 | 5/1966 | Wise. |
| 3,257,310 | 6/1966 | Plank et al.. |
| 3,437,587 | 4/1969 | Elbert et al.. |
| 3,682,996 | 8/1972 | Kerr. |
| 3,698,157 | 10/1972 | Allen et al.. |
| 4,016,218 | 4/1977 | Haag et al.. |
| 4,049,738 | 9/1977 | Young. |
| 4,060,568 | 11/1977 | Rodewald. |
| 4,086,287 | 4/1978 | Kaeding et al.. |
| 4,090,981 | 5/1978 | Rodewald. |
| 4,100,215 | 7/1978 | Chen. |
| 4,117,024 | 9/1978 | Kaeding. |
| 4,127,616 | 11/1978 | Rodewald. |
| 4,145,315 | 3/1979 | Rodewald. |
| 4,224,141 | 9/1980 | Morrison et al.. |
| 4,283,306 | 8/1981 | Herkes. |
| 4,326,994 | 4/1982 | Haag et al.. |
| 4,402,867 | 9/1983 | Rodewald. |
| 4,443,554 | 4/1984 | Dessau. |
| 4,465,886 | 8/1984 | Rodewald ........................ 585/475 |
| 4,477,583 | 10/1984 | Rodewald ........................ 585/475 |
| 4,487,843 | 12/1984 | Telford et al.. |
| 4,522,929 | 6/1985 | Chester et al.. |
| 4,548,914 | 10/1985 | Chu. |
| 4,559,314 | 12/1985 | Shihabi. |
| 4,843,057 | 6/1989 | D'Amore et al.. |
| 4,851,604 | 7/1989 | Absil et al.. |
| 4,927,979 | 5/1990 | Yamagishi et al.. |
| 4,950,835 | 8/1990 | Wang et al.. |
| 5,173,461 | 12/1992 | Absil et al.. |
| 5,321,183 | 6/1994 | Chang et al. .................... 585/475 |
| 5,349,113 | 9/1994 | Chang et al. .................... 585/475 |
| 5,349,114 | 9/1994 | Lago et al. ....................... 585/475 |
| 5,365,003 | 11/1994 | Chang et al. .................... 585/470 |
| 5,365,004 | 11/1994 | Beck et al. ...................... 585/475 |
| 5,367,099 | 11/1994 | Beck et al. ...................... 58/475 |
| 5,382,737 | 1/1995 | Beck et al. ...................... 585/475 |
| 5,403,800 | 4/1995 | Beck et al. ...................... 502/64 |
| 5,406,015 | 4/1995 | Beck et al. ...................... 585/475 |
| 5,455,213 | 10/1995 | Chang et al. .................... 502/63 |
| 5,475,179 | 12/1995 | Chang et al. .................... 585/475 |
| 5,476,823 | 12/1995 | Beck et al. ...................... 502/60 |
| 5,488,194 | 1/1996 | Beck et al. ...................... 585/475 |
| 5,495,059 | 2/1996 | Beck et al. ...................... 585/470 |
| 5,498,814 | 3/1996 | Chang et al. .................... 585/475 |
| 5,516,736 | 5/1996 | Chang et al. .................... 585/475 |
| 5,516,956 | 5/1996 | Abchandani et al. ............ 585/481 |

FOREIGN PATENT DOCUMENTS 0 296 582 A2  6/1988  European Pat. Off..

OTHER PUBLICATIONS

Nakajima et al., "p-Xylene-Selective Disproportionation of Toluene over a Modified Pentasil Type Zeolite", *Sekiyu Gakkaishi*, 35(2), 185–189 (1992). (No Month).

Hibino et al., "Shape-Selectivity over HZSM-5 Modified by Chemical Vapor Depostion of Silicon Alkoxide", *Journal of Catalysis*, 128, 551–558 (1991). (No Month).

Lago et al., "The Nature of the Catalytic Sites in HZSM-5 Activity Enhancement", *New Development in Zeolite Science Technology: Proceeding of the 7th International Zeolite Conference*, 677–684 (1986). (No Month).

Primary Examiner—Walter D. Griffin
Attorney, Agent, or Firm—Malcolm D. Keen; Peter W. Roberts

[57] ABSTRACT

There is provided a process for shape selective toluene disproportionation that involves contacting a feedstream which includes toluene under conversion conditions, with ZSM-5 that has been selectivated at least once with an organosilicon selectivating agent. The conversion conditions of the hydrocarbon conversion process provide a toluene conversion of at least 40 wt. %.

10 Claims, No Drawings

HIGH CONVERSION TOLUENE DISPROPORTIONATION WITH EX SITU SELECTIVATED ZEOLITE CATALYSTS

CROSS-REFERENCE TO RELATED APPLICATION

This application is a continuation-in-part of U.S. application Ser. No. 08/453,042, filed May 30, 1995, which, in turn, is a division of U.S. application Ser. No. 08/069,251, filed May 28, 1993, now U.S. Pat. No. 5,476,823, the entire disclosure of which is incorporated herein by reference.

This application is also a continuation-in-part of U.S. application Ser. No. 08/338,297, filed Nov. 14, 1994, now U.S. Pat. No. 5,495,059, which, in turn, is a division of U.S. application Ser. No. 08/069,255, filed May 28, 1993, now U.S. Pat. No. 5,403,800, the entire disclosure of which is incorporated herein by reference.

BACKGROUND

The present invention is directed to a shape-selective toluene disproportionation process over a selectivated ZSM-5 catalyst.

The term "shape-selective catalysis" describes the catalytic selectivities found in zeolites. The principles behind shape selective catalysis have been reviewed extensively, e.g., by N. Y. Chen, W. E. Garwood and F. G. Dwyer, *Shape Selective Catalysis in Industrial Applications*, 36, Marcel Dekker, Inc. (1989). Within a zeolite pore, hydrocarbon conversion reactions such as paraffin isomerization, olefin skeletal or double bond isomerization, oligomerization and aromatic disproportionation, alkylation or transalkylation reactions are governed by constraints imposed by the channel size. Reactant selectivity occurs when a fraction of the feedstock is too large to enter the zeolite pores to react; while product selectivity occurs when some of the products cannot leave the zeolite channels. Product distributions can also be altered by transition state selectivity in which certain reactions cannot occur because the reaction transition state is too large to form within the zeolite pores or cages. Another type of selectivity results from configurational constraints on diffusion where the dimensions of the molecule approach that of the zeolite pore system. A small change in the dimensions of the molecule or the zeolite pore can result in large diffusion changes leading to different product distributions. This type of shape selective catalysis is demonstrated, for example, in selective toluene disproportionation to para-xylene (p-xylene).

The production of para-xylene is typically performed by methylation of toluene or by toluene disproportionation over a catalyst under conversion conditions. Examples include the reaction of toluene with methanol, as described by Chen et al., *J. Amer. Chem. Soc.* 101, 6783 (1979), and toluene disproportionation, as described by Pines in *The Chemistry of Catalytic Hydrocarbon Conversions*, Academic Press, NY, 72 (1981). Such methods typically result in the production of a mixture including para-xylene, ortho-xylene, and meta-xylene (i.e., p-, m-, o-xylene). Depending upon the degree of selectivity of the catalyst for para-xylene (para-selectivity) and the reaction conditions, different percentages of para-xylene are obtained. The yield, i.e., the amount of xylene produced as a proportion of the feedstock, is also affected by the catalyst and the reaction conditions.

Various methods are known in the art for increasing the para-selectivity of zeolite catalysts. One such method is to modify the catalyst by treatment with a "selectivating agent." For example, U.S. Pat. Nos. 5,173,461; 4,950,835; 4,927,979; 4,465,886; 4,477,583; 4,379,761; 4,145,315; 4,127,616; 4,100,215; 4,090,981; 4,060,568; and 3,698,157 disclose specific methods for contacting a catalyst with a selectivating agent containing silicon ("silicon compound").

U.S. Pat. No. 4,548,914 describes another modification method involving impregnating catalysts with oxides which are difficult to reduce, such as those of magnesium, calcium, and/or phosphorus, followed by treatment with water vapor to improve para-selectivity.

European Patent No. 296,582 describes the modification of aluminosilicate catalysts by impregnating such catalysts with phosphorus-containing compounds and further modifying these catalysts by incorporating metals such as manganese, cobalt, silicon and Group IIA elements. The patent also describes the modification of zeolites with silicon compounds.

Traditionally, ex situ pre-selectivation of zeolites has involved single applications of the selectivating agent. It may be noted, however, that the suggestion of multiple treatments was made in U.S. Pat. No. 4,283,306 to Herkes. The Herkes patent discloses the promotion of crystalline silica catalyst by application of an amorphous silica such as ethylorthosilicate. The Herkes patent contrasts the performance of catalyst treated once with an ethylortho-silicate solution followed by calcination against the performance of catalyst treated twice with ethylorthosilicate and calcined after each treatment. The Herkes disclosure, however, shows that the twice-treated catalyst is less active and less selective than the once-treated catalyst as measured by methylation of toluene by methanol. Thus, Herkes indicates that multiple ex situ selectivation confers no benefit and in fact reduces a catalyst's efficacy in shape-selective reactions.

In U.S. Ser. No. 08/269,051, the first multiple ex situ selectivation sequence of catalytic molecular sieves to enhance selectivity in hydrocarbon conversion reactions was described. These catalysts proved particularly useful in toluene disproportionation as demonstrated in U.S. Pat. Nos. 5,365,004 and 5,367,099 which issued on the 15th and 22nd of Nov. 1994, respectively. The disclosures of U.S. Pat. Nos. 5,365,004 and 5,367,099 are herein incorporated by reference.

However, because para-isomers of alkyl-substituted aromatic hydrocarbons (e.g., para-xylene) can be utilized to produce a variety of commercial products, there is still a continuing need in the art to increase the efficiency of production.

Accordingly, it is an object of the present invention to improve the efficiency of producing alkyl substituted aromatic hydrocarbons, such as para-xylene, with ex situ selectivated catalytic molecular sieves.

SUMMARY

There is provided a process for continuously disproportionating toluene, said process comprising contacting toluene and hydrogen in the absence of a silicon containing selectivating agent cofeed with a catalyst under steady-state toluene disproportionation conditions at a temperature of 500° C. or less sufficient to convert at least 40% of said toluene, wherein said catalyst comprises ZSM-5 having a silica to alumina molar ratio of 60 or less, said catalyst being prepared by a method comprising the steps of:

(a) contacting said ZSM-5 under liquid phase conditions with an organosilicon selectivating agent under conditions sufficient to impregnate said molecular sieve with said organosilicon selectivating agent; and (b) calcining the impregnated molecular sieve of step (a) under conditions sufficient to decompose said organosilicon selectivating agent and leave a siliceous residue of said agent on said molecular sieve.

The present toluene disproportionation reaction is maintained continuously under steady-state conditions. It will be understood that the term steady-state connotes that the level of toluene conversion and the percentage of para-xylene in the total xylenes remain essentially constant for an extended period of time, e.g., for at least 3 days. This steady-state of operation is maintained by the use of a hydrogen cofeed and by avoiding the use of a silicon containing cofeed, as well as by operation at temperatures less than 500° C. At these low temperatures, particularly in the presence of a sufficient amount of hydrogen cofeed, the catalyst ages slowly without rapid coking.

The invention includes, inter alia, a process of shape-selective toluene disproportionation over a modified catalytic molecular sieve by contacting a reaction stream comprising toluene with a modified catalytic molecular sieve under high conversion conditions. Preferably, the hydrocarbon conversion process operates at a toluene conversion level of at least 40 wt. %. The toluene conversion level may even be greater than 45 wt. %

The modified catalytic molecular sieve is a catalytic molecular sieve that has been exposed to at least one ex situ selectivation sequence. Each ex situ selectivation sequence includes impregnating the catalytic molecular sieve with a selectivating agent, followed by calcination after each impregnation. Selectivating agents useful in the present invention include a large variety of silicon-containing compounds, and preferably include silicon polymers soluble in organic carriers. Such organic carriers include various alkanes, preferably paraffins having 6 or more carbons.

Through the utilization of ex situ selectivated zeolite catalysts, high conversion levels of toluene can be achieved while maintaining regioselectivity for the para-isomers at a level above equilibrium para-selectivity, if desired. More particularly, regioselectivity for para-xylene can maintained at a level above 24 wt. %. Moreover, the ex situ selectivated zeolite catalysts produce less $C_{9+}$ by-products than their non-selectivated counterparts at comparable high conversion rates. This in turn decreases the amount downstream processing required to remove such by-products. Advantageously, in the case of toluene disproportionation, the ability to maintain para-selectivity above equilibrium levels at such high conversion levels provides a cost-effective method of producing para-xylene. Accordingly, the present invention provides an improved process of shape-selective toluene disproportionation.

DETAILED DESCRIPTION

As previously described, multiply ex situ selectivated zeolite catalysts have been found to exhibit superior regioselectivity for the para-isomer in shape-selective hydrocarbon conversion reactions, such as toluene disproportionation. The superior regioselectivity exhibited by these catalysts was originally demonstrated at low to moderate hydrocarbon conversion levels. Generally, this was from 15 to 35 wt. % conversion of the aromatic hydrocarbon compound. It has now been found that ex situ selectivated zeolite catalysts also exhibit superior regioselectivity for the para-isomer at high conversion levels.

By reference to "high conversion levels," disproportionation reactions at a toluene conversion level of at least 40 wt. % are contemplated. Moreover, the present catalysts can be utilized in disproportionation reactions at toluene conversion levels up to 45 wt. % and higher while still providing above equilibrium para-selectivity. The ability to run these catalysts at such high conversion levels allows for their use as possible substitute catalysts in known hydrocarbon conversion reactions that require high conversion passes. One such process is the transalkylation method known as the "Taroray" process developed by Toray Industries, Inc., of Japan.

The presently selectivated zeolite catalysts have also been found to produce less $C_{9+}$ by-products than their non-selectivated counterparts at comparable high conversion runs. As is well known in the art, $C_{9+}$ by-products are difficult to process and must be converted to more useful species via transalkylation. Thus, there is a clear economic advantage in reducing the level of $C_{9+}$ production since less downstream processing will be required.

For the process of the present invention, a zeolite catalyst in bound or unbound form is impregnated at least once, e.g., two or three times, with a selectivating agent. The selectivating agent comprises a compound or polymer containing silicon. In order to facilitate a more controlled application of the selectivating agent, the selectivating agent can be dispersed in a carrier, particularly an aqueous and organic liquid carrier.

In each phase of the selectivation treatment, the selectivating agent is deposited on the external surface of the catalyst by any suitable method. For example, a selectivating agent may be dissolved in a organic carrier, mixed with the catalyst, and then dried by evaporation or vacuum distillation. This method is termed "impregnation". The molecular sieve may be contacted with the silicon compound at a molecular sieve/silicon compound weight ratio of from about 100/1 to about 1/100.

The silicon compound employed may be in the form of a solution or an emulsion under the conditions of contact with a zeolite. It is believed that the deposited silicon compound extensively covers, and resides substantially exclusively on, the external surface of the molecular sieve. Examples of methods of depositing silicon on the surface of the zeolite are found in U.S. Pat. Nos. 4,090,981; 5,243,117; and 5,403,800, as well as in U.S. application Ser. No. 08/062, 251, filed May 28, 1993, which are incorporated by reference herein.

As was described above, the catalysts useful in the present invention are ex situ selectivated by single or multiple coatings with a selectivating agent, each coating followed by calcination. Such selectivating agents include, for example, organic silicon compounds such as phenylmethyl silicone, dimethyl silicone, and blends thereof which have been found to be suitable.

Useful selectivating agents include siloxanes which can be characterized by the general formula:

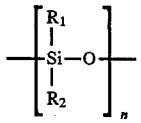

where $R_1$ is hydrogen, halogen, hydroxyl, alkyl, halogenated alkyl, aryl, halogenated aryl, aralkyl, halogenated aralkyl, alkaryl or halogenated alkaryl. The hydrocarbon substituents generally contain from 1 to 10 carbon atoms, preferably methyl, ethyl, or phenyl groups. $R_2$ is independently selected from the same group as $R_1$, and n is an integer of at least 2 and generally in the range of 3 to 1000. The molecular weight of the silicone compound employed is generally between about 80 and about 20,000 and preferably within the approximate range of 150 to 10,000. Representative silicone compounds include dimethyl silicone, diethyl silicone, phenylmethyl silicone, methylhydrogen-silicone, ethylhydrogen silicone, phenylhydrogen silicone, methylethyl silicone, phenylethyl silicone, diphenyl silicone, methyltrifluoropropyl silicone, ethyltri-fluoropropyl silicone, polydimethyl silicone, tetrachloro-phenylmethyl silicone, tetrachlorophenylethyl silicone, tetrachlorophenylhydrogen silicone, tetrachlorophenylphenyl silicone, methylvinyl silicone and ethylvinyl silicone. The silicone compound need not be linear, but may be cyclic, for example, hexamethyl cyclotrisiloxane, octamethyl cyclo-tetrasiloxane, hexaphenyl cyclotrisiloxane and octaphenyl cyclotetrasiloxane. Mixtures of these compounds may also be used, as may silicones with other functional groups.

Preferred silicon-containing selectivating agents include dimethylphenylmethyl polysiloxane (e.g., Dow-550), and phenylmethyl polysiloxane (e.g., Dow-710). Dow-550 and Dow-710 are available from Dow Chemical Co., Midland, Mich.

Preferably, the kinetic diameter of the para-selectivating agent is larger than the zeolite pore diameter, in order to avoid entry of the selectivating agent into the pore and any concomitant reduction in the internal activity of the catalyst.

Examples of suitable organic carriers for the selectivating silicon compound include hydrocarbons such as linear, branched, and cyclic alkanes having five or more carbons. In the methods of the present invention it is preferred that the carrier be a linear, branched, or cyclic alkane having a boiling point greater than about 70° C., and most preferably containing 6 or more carbons. Optionally, mixtures of low volatility organic compounds, such as hydrocracker recycle oil, may also be employed as carriers. Particular low volatility hydrocarbon carriers of selectivating agents are decane and dodecane.

It has been found that a multiple selectivation scheme provides unexpectedly increased efficiency of deposition of the silicon compound on the surface of the catalyst. This increased efficiency allows for the use of relatively small quantities of the silicon compound as well as relatively small quantities of the carrier. A more detailed discussion on the increased efficacy of depositing silicon compounds via multiply ex situ selectivation is described in U.S. Ser. No. 08/069,251, as well as in U.S. Pat. No. 5,403,800.

Following each deposition of the silicon compound, the catalyst is calcined to decompose the molecular or polymeric species to a solid state species. The catalyst may be calcined at a rate of from about 0.2° C./minute to about 5° C./minute to a temperature greater than 200° C., but below a temperature at which the crystallinity of the zeolite is adversely affected. Generally, such temperature will be below 600° C. Preferably the temperature of calcination is within the approximate range of 350° C. to 550° C. The product is maintained at the calcination temperature usually for 1 to 24 hours, preferably for between 2 and 6 hours.

The catalyst may be calcined in an atmosphere of $N_2$, an oxygen-containing atmosphere, preferably air, an atmosphere of $N_2$ followed by an oxygen-containing atmosphere, or an atmosphere containing a mixture of $N_2$ and air. Calcination should be performed in an atmosphere substantially free of water vapor, to avoid undesirable uncontrolled steaming of the silicon coated catalyst. The catalyst may be calcined once or more than once after each silicon deposition. The various calcinations in any impregnation sequence need not be identical, but may vary with respect to the temperature, the rate of temperature rise, the atmosphere and the duration of calcination.

Factors upon which the amount of silica incorporated with the zeolite is dependent include temperature, concentration of the silicon compound in the containing medium (the carrier material), the degree to which the zeolite has been dried prior to contact with the silicon compound, and calcination of the zeolite.

After the selectivation sequence, the catalyst may be subjected to steam treatment at a temperature of from about 100° C. to about 600° C., preferably from about 175° C. to about 325° C.; with from about 1% to about 100% steam, preferably from about 50% to about 100% steam; at a pressure of from about 0.01 psia to about 50 psia; for about two to about twelve hours, preferably from about three to about six hours. The selectivated molecular sieve catalyst can show improved selectivity upon steaming. Excessive steaming, however, can be detrimental to a selectivated catalyst.

In the present reaction toluene is fed in the absence of a selectivating agent. Therefore, the present process is distinguished from a process wherein the toluene may be fed simultaneously with a second selectivating agent and hydrogen at reaction conditions until the desired para-isomer selectivity is attained, whereupon the co-feed of selectivating agent is discontinued. This co-feeding of selectivating agent with alkylaromatic is one type of "trim-selectivation." Reaction conditions for this in situ trim-selectivation step generally include a temperature of from about 350° C. to about 540° C. and a pressure of from about atmospheric to about 5000 psig. The reaction stream is fed to the system at a rate of from about 0.1 WHSV to about 20 WHSV. Hydrogen may be fed at a hydrogen to hydrocarbon molar ratio of from about 0.1 to about 20.

The present reaction takes place under conditions wherein trim-selectivation is avoided. The selectivating agent for trim-selectivation may comprise a silicon compound discussed in greater detail above. For example, organic silicon compounds such as phenylmethyl silicone, dimethyl silicone, and mixtures thereof are suitable. According to one embodiment of trim-selectivation, a silicone containing phenylmethyl silicone and dimethyl silicone groups in a ratio of about 1:1 is co-fed to the system, while the other components, e.g., alkylaromatic and hydrogen, are fed in the amounts set forth above. The selectivating agent is fed in an amount of from about 0.001 wt. % to about 10 wt. % of the alkylaromatic according to this preferred embodiment. Depending upon the percentage of selectivating agent used, the trim-selectivation will last for at least one hour, preferably about 1 to about 48 hours, most preferably less than 24 hrs.

In this scheme the silicon compound will decompose to deposit additional silica onto the catalyst. During the trim-selectivation procedure the para-selectivity of the catalyst will be observed to increase further. The silicon-containing polymer or molecular species may be dissolved in toluene or another appropriate hydrocarbon carrier.

Another form of trim-selectivation to be avoided in the present toluene disproportionation reaction is trim-selectivation with a thermally decomposable organic compound at an elevated temperature in excess of the decomposition temperature of the compound but below the temperature at which crystallinity of the zeolite is adversely affected. Generally, this temperature will be greater than 500° C., but less than about 650° C.

Organic materials, thermally decomposable under the above temperature conditions to provide coke trimming, encompass a wide variety of compounds including by way of example, hydrocarbons, such as paraffinic, cycloparaffinic, olefinic, cycloolefinic and aromatic; oxygen-containing organic compounds such as alcohols, aldehydes, ethers, ketones and phenols; heterocyclics such as furans, thiophenes, pyrroles and pyridines. Usually, it is contemplated that a thermally decomposable hydrocarbon, such as an alkyl-substituted aromatic, will be the source of coke, most preferably the alkylaromatic being subjected to disproportionation itself. In the latter case, the alkylaromatic is initially brought into contact with the catalyst under conditions of temperature and hydrogen concentration amenable to rapid coke formation. Typically, coke trimming is conducted at conditions outside the operating parameters used during the main time span of the catalytic cycle. When the desired coke deposition has been effected, the alkylaromatic feed is continued in contact with the coke-containing catalyst under conditions of temperature and hydrogen concentration conducive to disproportionation, with a greatly reduced coking rate.

The catalytic molecular sieves useful in accordance with the methods of the present invention are preferably in the hydrogen form prior to modification, but may be in the ammonium or sodium form. Preferably, the catalytic molecular sieve is as discussed above. ZSM-5 is described, for example, in U.S. Pat. Nos. 3,702,886 and Re. No. 29,949.

The crystal size of zeolites used herein is preferably greater than 0.1 micron, e.g., from 0.1 to 1 micron, e.g., from 0.1 to 0.5 micron. The accurate measurement of crystal size of zeolite materials is frequently very difficult. Microscopy methods, such SEM and TEM, are often used, but these methods require measurements on a large number of crystals and for each crystal measured, values may be required in up to three dimensions. For ZSM-5 materials described in the examples below, estimates were made of the effective average crystal size by measuring the rate of sorption of 2,2-dimethylbutane at 90° C. and 60 torr hydrocarbon pressure. The crystal size is computed by applying the diffusion equation given by J. Crank, "The Mathematics of Diffusion", Oxford at the Clarendon Press, 1957, pp 52–56, for the rate of sorbate uptake by a solid whose diffusion properties can be approximated by a plane sheet model. In addition, the diffusion constant of 2,2-dimethylbutane, D, under these conditions is taken to be $1.5 \times 10^{-14}$ cm$^2$/sec. The relation between crystal size measured in microns, d, and diffusion time measured in minutes, $t_{0.3}$, the time required for the uptake of 30% of capacity of hydrocarbon, is:

$$d = 0.0704 \times t_{0.3}^{1/2}.$$

In the present case these measurements have been made on a computer controlled, thermogravimetric electrobalance, but there are numerous ways one skilled in the art could obtain the data. The larger crystal material used herein has a sorption time, $t_{0.3}$, of 497 minutes, which gives a calculated crystal size of 1.6 microns. The smaller crystal material has a sorption time of 7.8 minutes, and a calculated crystal size of 0.20 micron.

The "alpha value" of a catalyst is an approximate indication of the catalytic cracking activity of the catalyst compared to a standard catalyst, and it gives the relative rate constant (rate of normal hexane conversion per volume of catalyst per unit time). It is based on the activity of the amorphous silica-alumina cracking catalyst taken as an alpha of 1 (Rate Constant=0.016 sec$^{-1}$). The alpha test is described in U.S. Pat. No. 3,354,078 and in the *Journal of Catalysis*, 4, 522–529 (1965); 6, 278 (1966); and 61, 395 (1980), each incorporated herein by reference as to that description. It is noted that intrinsic rate constants for many acid-catalyzed reactions are proportional to the alpha value for a particular crystalline silicate catalyst (see "The Active Site of Acidic Aluminosilicate Catalysts," *Nature*, 309, No. 5959, 589–591, (1984). The experimental conditions of the test used herein include a constant temperature of 538° C. and a variable flow rate as described in detail in the *Journal of Catalysis*, 61, 395 (1980). The catalyst in the present invention preferably has an alpha value greater than 1, for example, from about 1 to about 2000. The alpha value of the catalyst may be increased by initially treating the catalyst with nitric acid or by mild steaming before pre-selectivation. This type of steaming is discussed in U.S. Pat. No. 4,326,994.

The catalysts of the present invention may optionally be employed in combination with a support or binder material (binder). The binder is preferably an inert, non-alumina containing material, such as a porous inorganic oxide support or a clay binder. One such preferred inorganic oxide is silica. Other examples of such binder materials include, but are not limited to, zirconia, magnesia, titania, thoria and boria. These materials may be utilized in the form of a dried inorganic oxide gel or as a gelatinous precipitate. Suitable examples of clay binder materials include, but are not limited to, bentonite and kieselguhr. The relative proportion of catalyst to binder material to be utilized is from about 30 wt. % to about 98 wt. %. A proportion of catalyst to binder from about 50 wt. % to about 80 wt. % is more preferred. The bound catalyst may be in the form of an extrudate, beads or fluidizable microspheres.

The silica to alumina ratio (SiO$_2$/Al$_2$O$_3$) of the catalysts of the invention may be determined by conventional analysis. This ratio is meant to represent, as closely as possible, the ratio in the rigid atomic framework of the zeolite crystal and to exclude aluminum in the binder or in cationic or other form within the channels. The silica to alumina ratio of the present ZSM-5 may be less than 60, e.g., from 20 to 40.

While not wishing to be bound by theory, it is believed that the advantages of multiply ex situ selectivation are in part obtained by rendering acid sites on the external surfaces of the catalyst substantially inaccessible to reactants, while increasing catalyst tortuosity. Acid sites existing on the external surface of the catalyst are believed to isomerize the solution-phase para-isomer back to an equilibrium level with the other two isomers. In the case of xylene production, for example, the amount of para-xylene in the total xylene yield is reduced to about 24 wt. %, i.e., equilibrium para-selectivity. Thus, by reducing the availability of these acid sites to the solution-phase para-xylene, the relatively high proportion of para-xylene can be maintained. It is believed that the para-selectivating agents of the present invention block or otherwise render these external acid sites unavailable to the para-isomers by chemically modifying these sites.

Particularly when the multiply selectivated versions of the present ZSM-5 catalysts are used, the para-selectivity of the present toluene disproportion may be greater than 30% e.g., at least 40%.

TOLUENE DISPROPORTIONATION

Normally a single pass conversion of an alkylbenzene stream results in a product stream which includes dialkylbenzenes having alkyl groups at all locations, i.e., o-, m-, and p-dialkylbenzenes. A catalyst treated in the manner described herein exhibits a desirable decreased ortho-dialkylbenzene sorption rate parameter. For example, diffusion rate constants in toluene disproportionation have been discussed by D. H. Olson and W. O. Haag, "Structure- Selectivity Relationship in Xylene Isomerization and Selective Toluene Disproportionation", *Catalytic Materials: Relationship Between Structure and Reactivity*, ACS Symposium Ser. No. 248 (1984).

In toluene disproportionation, toluene diffuses into the zeolite with a diffusivity $D_T$. The toluene undergoes disproportionation to p-, m-, and o-xylene and benzene at a total rate constant $k_D$. For high selectivity and catalyst efficiency it is desirable to have $$k_D \ll \frac{D_T}{r_2}.$$

The degree of para-selectivity depends on the activity and the diffusion characteristics of the catalyst. The primary product will be rich in the para isomer if initially produced m- and o-xylene diffuse out of the zeolite crystal at a rate $(D_{m,o}/r^2)$ that is lower than that of their conversion to p-xylene $(k_I)$, as well as lower than that of the p-xylene diffusion $(D_p/r^2)$ out of the catalyst, where:

$D_m$=diffusion of m-xylene;

$D_o$=diffusion of o-xylene;

$D_p$=diffusion of p-xylene;

r=length of diffusion path (crystal size);

$k_I$=rate of interconversion via isomerization of xylene isomers yielding secondary xylene product m-xylene and o-xylene.

It is desirable to increase the para-selectivity of the catalyst. Practically, this involves decreasing the o- and m-xylene diffusivities such that $$k_I > \frac{D_{m,o}}{r^2}.$$

In such a case the rate of conversion of m- and o-xylenes to p-xylene exceeds the diffusivities of the m- and o-xylenes. As a result, the proportion of the xylene yield that is p-xylene will be increased. Those skilled in the art will appreciate that similar considerations apply to the diffusivities of other alkylbenzenes.

The production stream will also contain small amounts of o- and m-xylene and trace amounts of impurities such as ethylbenzene and $C_{9+}$ by-products. The amount of these undesirable products can become greater as the conversion of toluene increases. As previously described, however, the catalysts of the present invention surprisingly exhibit reduced production levels of $C_{9+}$ by-products in comparison to the non-selectivated counterparts.

As used herein, the term "para-xylene selectivity" means the proportion of p-xylene, indicated as a percentage, among all of the xylene products, i.e., p-xylene, o-xylene, and m-xylene. Those skilled in the art will appreciate that the relative proximity of the boiling points of these xylene isomers necessitates relatively expensive separation processes for the isolation of p-xylene. On the other hand, p-xylene is more readily separated from other components in the product stream such as benzene, toluene, and p-ethyltoluene.

Furthermore, the alkylbenzenes are known to proceed in reactions which produce unwanted heavier alkylbenzenes. For example, the xylenes can react to produce unwanted ethylbenzenes by the following reaction:

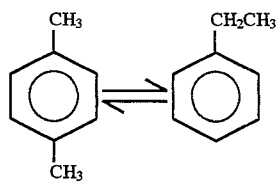

The toluene feedstock preferably includes about 50% to about 100% toluene, more preferably at least about 80% toluene. Other compounds such as benzene, xylenes, and trimethylbenzene may also be present in the toluene feedstock without adversely affecting the present invention.

Operating conditions employed in the process of the present invention will affect the para-selectivity and toluene conversion levels. Such conditions include the temperature, pressure, space velocity, molar ratio of the reactants, and the hydrogen to hydrocarbon mole ratio ($H_2$/HC). It has also been observed that an increased space velocity (WHSV) can enhance the para-selectivity of the modified catalyst in alkylbenzene disproportionation reactions. However, with an increase in WHSV a decrease in the hydrocarbon conversion level is usually observed. This characteristic of the modified catalyst allows for substantially improved throughput when compared to current commercial practices. In addition, it has been observed that the disproportionation process may be performed using $H_2$ as a diluent, thereby dramatically increasing the cycle length of the catalyst.

In accordance with the present invention, toluene conversion via disproportionation is achieved at conversion level of at least 40 wt. %. At such high levels of toluene conversion, para-selectivity will decrease, in comparison to lower conversion levels, but can remain above equilibrium para-selectivity, i.e., 24 wt. %. For example, one skilled in the art can expect that the para-selectivity to decrease to a level approaching equilibrium para-selectivity when toluene conversion levels are pushed to 45–50 wt. %. However, with the multiply selectivated versions of the present catalyst, reaction conditions can easily be varied to maintain high conversion levels with equilibrium or above-equilibrium para-selectivity.

The selectivated catalytic molecular sieve can be contacted with a toluene feedstock under conditions for effecting vapor-phase disproportionation. Conditions effective for accomplishing the high para-selectivity and acceptable toluene disproportionation conversion levels include a reactor inlet temperature of from about 200° C. to about 500° C., preferably from 350° C. to about 500° C.; a pressure of from about atmospheric to about 5000 psia, preferably from about 100 to about 1000 psia; a WHSV of from about 0.1 to about 20, preferably from about 2 to about 10; and a $H_2$/HC mole ratio of from about 0.1 to about 20, e.g., from about 0.5 to about 6, e.g., 1 or greater. This process may be conducted in either batch or fluid bed operation, with the attendant benefits of either operation readily obtainable. The effluent may be separated and distilled to remove the desired product, i.e., p-xylene, as well as other by-products. Alternatively, the $C_8$ fraction may be subjected to further separation, as in the case of xylenes, subjected to crystallization or the PAREX process to yield p-xylene.

The catalyst may be further modified in order to reduce the amount of undesirable by-products, particularly ethylbenzene. The state of the art is such that the reactor effluent from standard toluene disproportionation typically contains about 0.5 wt. % ethylbenzene by-product. Upon distillation of the reaction products, the level of ethylbenzene in the $C_8$ fraction often increases to between about 3 wt. % and 4 wt.

%. This level of ethylbenzene is unacceptable for polymer grade p-xylene, since ethylbenzene in the p-xylene product, if not removed, degrades the quality of fibers ultimately produced from the p-xylene product. Consequently, ethylbenzene content of the p-xylene product must be kept low. The specification for the allowable amount of ethylbenzene in the p-xylene product has been determined by the industry to be less than 0.3 wt. %. Ethylbenzene can be substantially removed by crystallization, by selective sorption or by superfractionation processes.

In order to avoid the need for downstream ethylbenzene removal, the level of ethylbenzene by-product is advantageously reduced by incorporating a hydrogenation/dehydrogenation function within the catalyst, such as by addition of a metal compound such as platinum. While platinum is the preferred metal, other metals of Groups IB to VIII of the Periodic Table such as palladium, nickel, copper, cobalt, molybdenum, rhodium, ruthenium, silver, gold, mercury, osmium, iron, zinc, cadmium, and mixtures thereof, may be utilized. The metal may be added by cation exchange, in amounts of from about 0.001 wt. % to about 2 wt. %, typically about 0.5 wt. %. For example, a platinum modified catalyst can be prepared by first adding the catalyst to a solution of ammonium nitrate in order to convert the catalyst to the ammonium form. The catalyst is subsequently contacted with an aqueous solution of tetraamine platinum (II) nitrate or tetraamine platinum(II) chloride. The catalyst can then be filtered, washed with water and calcined at temperatures of from about 250° C. to about 500° C. It will be appreciated by those skilled in the art that similar considerations apply to processes involving alkylbenzenes other than toluene.

EXAMPLES

The following non-limiting Examples illustrate the invention in relation to the disproportionation of toluene as well as in relation to the similar disproportionation of ethylbenzene.

Example 1

A steamed control catalyst was prepared by steaming ZSM-5/Al$_2$O$_3$ (65% ZSM-5/35% Al$_2$O$_3$) with 100% water vapor at approximately 750° F.(399° C.) for approximately 4 hours.

Example 2

A once-selectivated catalyst (1X) was prepared by contacting a batch of H-ZSM-5/SiO$_2$ with a 7.8 wt. % solution of dimethylphenylmethyl polysiloxane (Dow-550) in decane. The decane solvent was stripped of the catalyst. The catalyst was then calcined in a muffle furnace under N$_2$, followed by air. The temperature of the furnace was elevated gradually at 2° C./min. until 538° C. and maintained at that temperature.

Example 3

A twice-selectivated catalyst (2X) was prepared by contacting a sample of H-ZSM-5A/SiO$_2$ (65% H-ZSM-5/35% SiO$_2$) with a 7.8 wt. % solution of Dow-550 in decane and subsequently calcined following the procedure described in Example 2. The selectivation process was repeated to obtain a twice selectivated catalyst.

Example 4

A three-times selectivated catalyst (3X) was prepared by contacting a sample of H-ZSM-5/SiO$_2$ (65% H-ZSM-5/35% SiO$_2$) with a 7.8 wt. % solution of Dow-550 in decane and subsequently calcining the catalyst following the procedure described in Example 2. The selectivation process was repeated twice to obtain a three-times selectivated catalyst.

Comparative Toluene Disproportionation Runs

Example 5

Toluene Disproportionation runs utilizing the catalysts prepared in Examples 1–4 and an unmodified ZSM-5/SiO$_2$ bound catalyst were conducted with an automated unit. The unit has an automated sampling feature with on-line gas chromatography (GC) for characterization of the entire product effluent. Approximately one gram of each of the catalyst samples were individually loaded into 0.25 diameter, stainless steel tube reactors and then placed into the automated unit. The catalysts was then heated to reaction temperature under N$_2$.

Each catalytic run was initiated with a pure toluene feed at a H$_2$/HC ratio of 1, a weight hourly space velocity of 6. The temperature of each run was varied to obtain a toluene conversion level of approximately 48 wt. %. After various time periods on stream, samples of the reactor effluent were taken and analyzed. The product composition of these samples as ascertained by GC analysis and the reaction conditions at the time these samples were taken are shown in Table 1.

TABLE 1

|  | Steamed | Un-steamed | 3X | 2X | 1X |
| --- | --- | --- | --- | --- | --- |
| CONDITIONS: |  |  |  |  |  |
| Temp. (°C.) | 457 | 432 | 474 | 461 | 444 |
| Press. (psig.) | 396 | 397 | 398 | 401 | 399 |
| WHSV (1/H) | 6 | 6 | 6 | 6 | 6 |
| H2/HC | 1 | 1 | 1 | 1 | 1 |
| TOS(H) | 11 | 24 | 12 | 53 | 4 |
| PRODUCT YIELD (wt. %): |  |  |  |  |  |
| C$_{5-}$ | 1.2 | 1.5 | 4.6 | 2.6 | 1.5 |
| Benzene | 20.7 | 20.7 | 24.2 | 21.6 | 21.0 |
| Toluene | 52.2 | 52.0 | 51.7 | 51.4 | 52.4 |
| Ethylbenzene | 0.5 | 0.5 | 1.2 | 0.7 | 0.6 |
| Para-Xyl | 5.2 | 5.1 | 6.9 | 5.6 | 5.2 |
| Meta-Xyl | 11.4 | 11.3 | 7.2 | 11.2 | 11.4 |
| Ortho-Xyl | 5.1 | 4.9 | 1.6 | 4.2 | 4.9 |
| C$_{9+}$ | 3.6 | 3.7 | 2.5 | 2.7 | 3.0 |
| Total Xyl. | 21.7 | 21.3 | 15.7 | 21.0 | 21.6 |
| Ben/Xyl | 1.3 | 1.3 | 2.1 | 1.4 | 1.3 |
| Para-Xylene Selectivity | 24.0 | 23.9 | 44.0 | 26.7 | 24.1 |
| Toluene Conv. | 47.7 | 48.0 | 48.3 | 48.6 | 47.6 |

From Table 1 it is readily apparent that the multiply-selectivated catalysts exhibited an increase in para-selectivity, in addition to a decrease in C$_{9+}$ production, when compared to their non-selectivated counterparts. At approximately 48 wt. % toluene conversion, the 3X sample exhibited a para-selectivity of 44 wt. % while the non-selectivated and singly selectivated samples exhibited a para-selectivity of only 24 wt. %, i.e., equilibrium para-selectivity. The 3X, 2X and 1X samples also exhibited a significant decrease in C$_{9+}$ production in comparison to the non-selectivated catalysts (2.5%, 2.7% & 3.0% versus 3.6% and 3.7%). The 2X sample also exhibited a para-selectivity above equilibrium para-selectivity while at the same exhibiting a decrease in C$_{9+}$ production. Accordingly, at hydrocarbon conversions above 35 wt. %, the selectivated catalysts of the present invention provide distinct advantages over their prior art counterparts.

Example 6

In order to further illustrate the advantages of the multiply-selectivated catalysts at high conversion levels, a sample of the 3X catalyst batch was evaluated at various operating temperatures. The reaction conditions, except for toluene conversion, were kept constant. After various time periods on-stream, samples of the reactor effluent were taken and analyzed. The product composition of these samples as ascertained by GC analysis and the reaction conditions at the time these samples were taken are shown in Table 2.

TABLE 2

| CONDITIONS: | | | | |
|---|---|---|---|---|
| Temp (°C.) | 416 | 449 | 469 | 489 |
| $H_2$/HC | 1 | 1 | 1 | 1 |
| Press (psig) | 271 | 270 | 270 | 271 |
| WHSV (1/Hr) | 3 | 3 | 3 | 3 |
| PRODUCT YIELD (wt. %): | | | | |
| $C_{5-}$ | 0.6 | 2.0 | 3.3 | 5.1 |
| Benzene | 13.3 | 20.0 | 23.5 | 26.9 |
| Ethylbenzene | 0.3 | 0.7 | 1.0 | 1.3 |
| Xylenes | 15.1 | 17.0 | 16.1 | 14.7 |
| Para Xylene | 9.7 | 8.8 | 7.4 | 6.3 |
| Para-Xylene Selectivity | 64.3 | 51.8 | 46.3 | 42.2 |
| Toluene Conv. | 29.7 | 40.8 | 45.6 | 49.4 |

As illustrated in Table 2, the three-times selectivated catalyst (3X) exhibited superior para-selectivity at toluene conversion levels over 35 wt. %. At a toluene conversion level of 40.8 wt. %, a 115% improvement over equilibrium para-selectivity was measured (i.e., {[51.8−24.0]/24.0}× 100%). As the conversion level reached 45.6 wt. %, a 93% improvement in para-selectivity was observed. Finally, at a conversion level of 49.4 wt. %, a 76% improvement in para-selectivity was observed. Thus, the multiply-selectivated catalysts exhibited excellent para-selectivity levels at high toluene conversion levels.

Thus, from the above examples the excellent performance of the selectivated catalysts at conversion levels above 35 wt. % is readily apparent. The multiply-selectivated catalysts exhibited para-selectivity levels greater than equilibrium para-selectivity, i.e., 24 wt. %. The prior art catalysts, however, only exhibited equilibrium para-selectivity. The performance exhibited by the present catalysts, in turn, makes the catalysts attractive as a substitute catalyst in high conversion methods, such as the Tatoray process. Moreover, the catalysts of the present invention provide the advantage of decreased $C_{9+}$ production, which reduces the amount of further downstream processing required. As a result of the present invention, the skilled artisan can now achieve high hydrocarbon conversion with greatly improved regioselectivity for the para-isomer, e.g., para-xylene in toluene disproportionation.

We claim:

1. A process for continuously disproportionating toluene, said process comprising contacting toluene and hydrogen in the absence of a silicon containing selectivating agent cofeed with a catalyst under steady-state toluene disproportionation conditions at a temperature of 500° C. or less sufficient to convert at least 40% of said toluene, wherein said catalyst comprises ZSM-5 having a silica to alumina molar ratio of 60 or less, said catalyst being prepared by a method comprising the steps of:

(a) contacting said ZSM-5 under liquid phase conditions with an organosilicon selectivating agent under conditions sufficient to impregnate said molecular sieve with said organosilicon selectivating agent; and (b) calcining the impregnated molecular sieve of step (a) under conditions sufficient to decompose said organosilicon selectivating agent and leave a siliceous residue of said agent on said molecular sieve, wherein steps (a) and (b) are repeated at least once, and wherein the toluene disproportionation product comprises greater than 30% para-xylene, based on the total xylene isomers.

2. The method of claim 1, wherein said conversion conditions provide a toluene conversion level of at least about 45 wt. %.

3. The process of claim 1, wherein said selectivating agent is selected from the group consisting of silicones, silicone polymers, silanes, and alkoxysilanes.

4. The process of claim 1, wherein said selectivating agent comprises dimethylphenylmethyl polysiloxane.

5. The process of claim 1, wherein said selectivating agent is dispersed in an organic carrier.

6. The process of claim 5, wherein said organic carrier is a paraffin containing at least 6 carbon atoms.

7. The process of claim 1, wherein steps (a) and (b) are repeated twice, and wherein the toluene disproportionation product comprises greater than 40% paraxylene, based upon the total xylene isomers.

8. The process of claim 1, wherein said ZSM-5 has a silica to alumina molar ratio of 20 to 40, and wherein at least 45% of said toluene is converted.

9. The process of claim 1, wherein said catalyst further comprises a binder, and wherein said catalyst is in the form of an extrudate.

10. The process of claim 1, wherein the hydrogen to toluene mole ratio in the reaction feed is 1 or greater.

* * * * *